United States Patent [19]

Hsu

[11] Patent Number: 4,580,566

[45] Date of Patent: Apr. 8, 1986

[54] ACUPUNCTURE NEEDLE AND NEEDLE GUIDE ASSEMBLY

[76] Inventor: John J. Hsu, 7224 Old Mill Rd., Birmingham, Mich. 48010

[21] Appl. No.: 665,290

[22] Filed: Oct. 26, 1984

Related U.S. Application Data

[63] Continuation-in-part of Ser. No. 370,682, Apr. 22, 1982, Pat. No. 4,479,496.

[51] Int. Cl.$^4$ .............................................. A61B 17/34
[52] U.S. Cl. ................................................. 128/329 A
[58] Field of Search ............... 128/329 R, 329 A, 314, 128/315, 361; 604/46, 199, 22

[56] References Cited

U.S. PATENT DOCUMENTS

| | | | |
|---|---|---|---|
| 2,857,912 | 10/1958 | Feinstone et al. | 128/215 |
| 3,875,944 | 4/1975 | Toyama | 128/303.1 |
| 3,905,373 | 9/1975 | Toyama | 128/329 A |
| 3,943,932 | 3/1976 | Woo | 128/303.18 |
| 4,139,011 | 2/1979 | Benoit et al. | 128/329 R |
| 4,154,342 | 5/1979 | Wallace | 206/439 |
| 4,161,943 | 7/1979 | Nogier | 128/1.3 |
| 4,262,672 | 4/1981 | Kief | 128/329 A |
| 4,479,496 | 10/1984 | Hsu | 604/329 A |

Primary Examiner—C. Fred Rosenbaum
Assistant Examiner—Michelle N. Lester
Attorney, Agent, or Firm—Gifford, Groh, Van Ophem, Sheridan, Sprinkle & Dolgorukov

[57] ABSTRACT

An acupuncture needle guide assembly includes a needle affixed to a handle which frictionally engages a tubular housing encasing the needle. The housing can be withdrawn from the needle only in a direction opposite the point of the needle. A guide member is insertably received in an open end of the housing opposite its engagement with the needle handle. The guide member includes a passage coaxial with the needle to permit the longitudinal movement of the needle through the guide member. The guide member separates into two detached halves upon removal of the housing, so that the entire guide and housing can be removed from the needle while the needle remains inserted in the skin.

15 Claims, 7 Drawing Figures

U.S. Patent  Apr. 8, 1986  Sheet 1 of 2  4,580,566
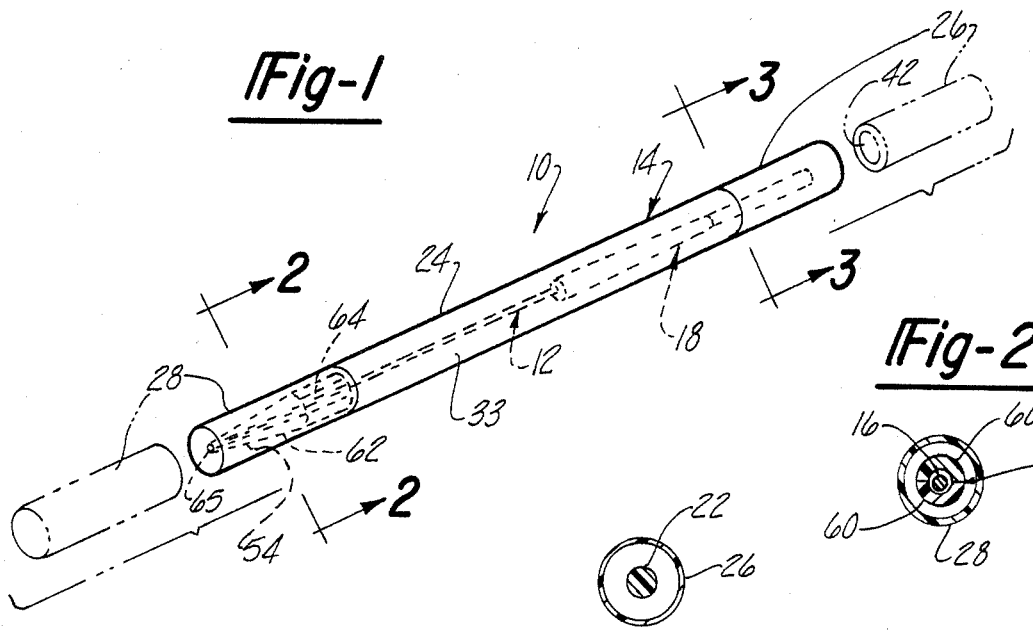
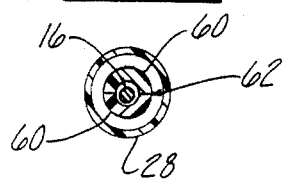
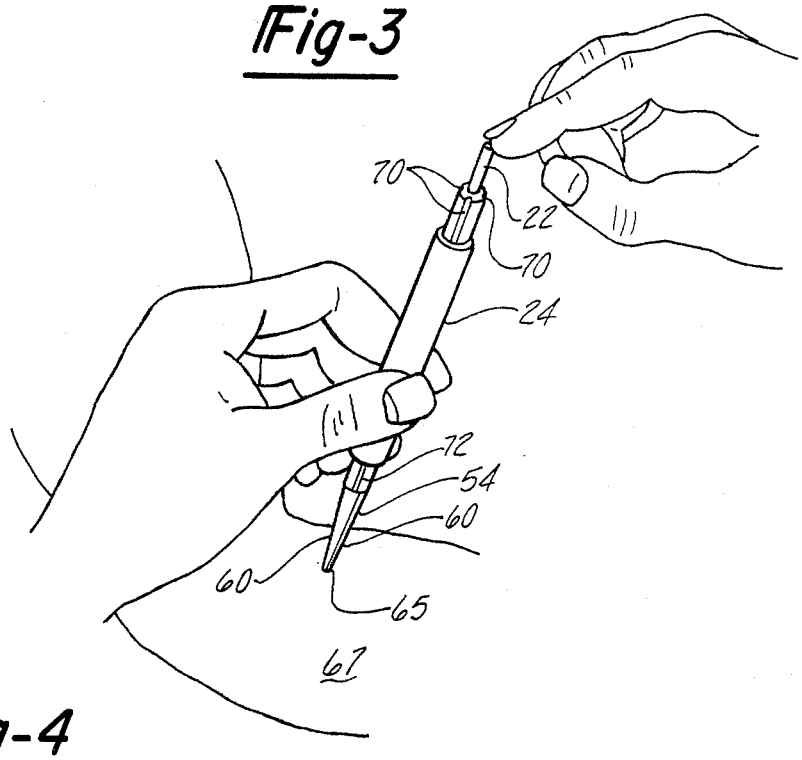

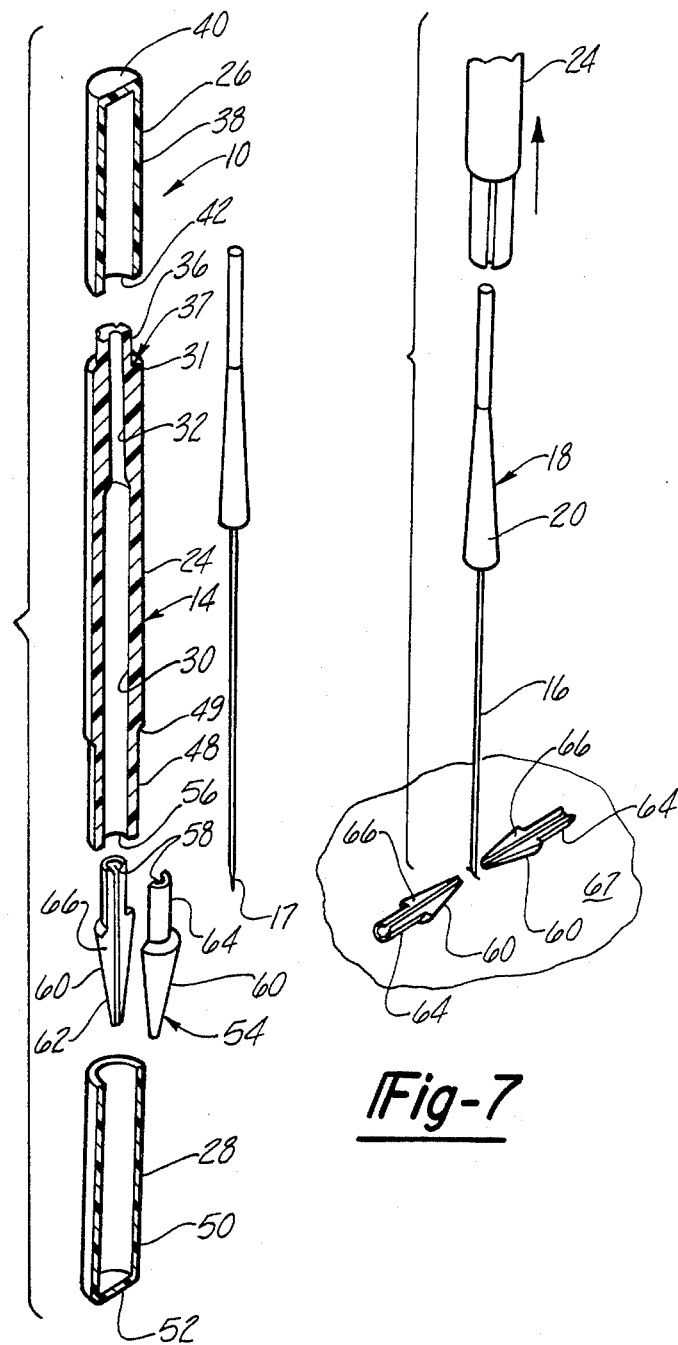
Fig-6
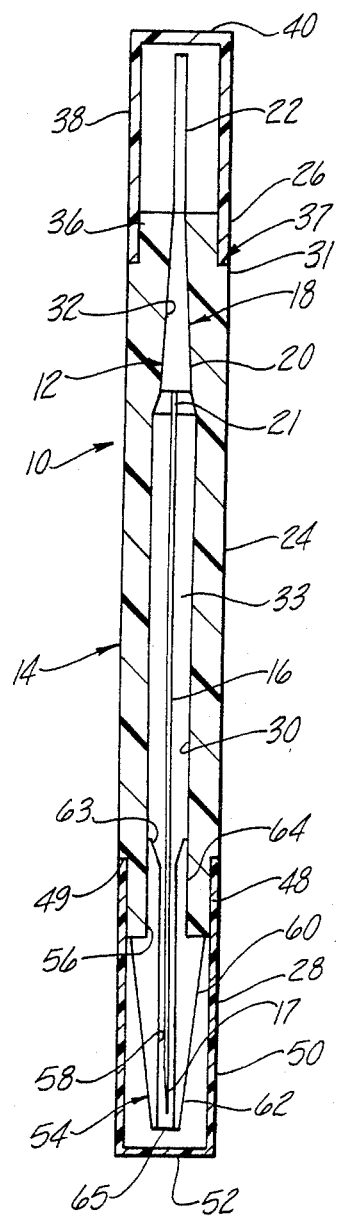
Fig-5

ACUPUNCTURE NEEDLE AND NEEDLE GUIDE ASSEMBLY

CROSS REFERENCE TO RELATED APPLICATION

This application is a continuation-in-part of my co-pending U.S. application Ser. No. 370,682, filed Apr. 22, 1982, now. U.S. Pat. No. 4,479,496, issued Oct. 30, 1984.

BACKGROUND OF THE INVENTION

I. Field of the Invention

The present invention relates generally to medical devices for puncturing the skin and more particularly to an acupuncture needle and applicator therefor which provides accurate placement of the needle, ease of insertion, maintains the sterility of the needle before the insertion into the skin, and is readily removable from the placed needle.

II. Description of the Prior Art

Acupuncture has gained increasing acceptance as a medical treatment. The treatment involves the insertion of needles into the skin of a patient at various areas of the body. Typically, the needles are filiform structures, having a length sufficient to permit a portion of the needle to be embedded in the skin to a depth sufficient to produce maximum effect of the treatment and a portion which remains protruded from the skin so that the needle can be removed when the treatment is completed. While these filiform needles can be inserted by skillful hands without additional aid, and can be sterilized to reduce the risk of infection by contamination of the needles, they require extreme care to be protected from contamination before and during their use. Moreover, due to the extremely small diameter and relative long length of these needles, insertion and manipulation of the needles by hand can be difficult. In order to overcome these disadvantages, applicators have been developed which encase the needle and provide a mechanism for releasing the needle from the applicator and inserting it into the skin. One of the previously known types of applicators includes a plunger mechanism for projecting the needle from the enclosure. Such a structure employs numerous parts and is thus quite complicated and expensive to produce.

Another known type of projector applicator is disclosed in U.S. Pat. No. 3,905,375 to Toyama. That patent discloses a needle having an enlarged diameter shank portion which is encased in a pair of tubular members. The ends of the first tube are enclosed by rupturable membranes, and the tube is slidably insertable into the second tube. The second tube has a closed end which abuts against the axial end of the shank of the needle. To discharge the needle, the second tube is depressed over the first tube so as to urge the needle through the rupturable membranes towards the skin of the patient. However, such a device is disadvantageous for the reason that during handling or transportation, the outer tube can be inadvertently depressed over the inner tube, and cause the needle to protrude through the rupturable membrane and become exposed after sterilization. More importantly, since both the needle and the shank of the needle must pass through the membrane in order to remove the applicator from the needle, portions of the membrane may contaminate the site of insertion of the needle. The open end of the shield may not adequately protect the needle from contamination. The ruptured membrane can cause friction between the handle and the shield during the insertion and removal of the shield and plunger assembly, and can possibly pull the needle out of the skin during the process of removal of the assembly.

SUMMARY OF THE PRESENT INVENTION

The present invention overcomes these and other disadvantages by providing an acupuncture needle and needle guide assembly including a filiform needle having an enlarged diameter handle opposite the needle point, together with a tubular housing having a bore portion at one end which slidably receives a portion of the handle of the needle. The bore portion of the tube supports the needle within a needle enclosing chamber formed by a second elongated housing portion on one side of the housing bore portion. At least part of the needle handle extends outwardly from the other side of the housing bore portion.

A guide member is insertably received in an open end of the tubular housing opposite the housing bore portion. The guide member includes a guide passage portion formed therein, coaxial with the encased needle. The guide member comprises a plurality of split member portions, preferably a pair of guide member half portions. The portions are retained in abutment by the insertion of the guide member in the open end of the tubular housing. The guide member preferably comprises a conical portion coaxial with the passage portion, affixed to a stem portion, the stem portion being insertable into the open end of the tubular housing.

Preferably, the ends of the tubular member include reduced diameter portions which slidably receive end caps thereon, and include abutment surfaces against which the ends of the end caps can rest. Apertures are provided in the abutment surface for the passage of sterlizing steam to the interior of the needle guide assembly.

In addition, the housing bore portion preferably includes means for limiting the sliding displacement of the handle in a direction away from the elongated housing portion, and this is conveniently accomplished by a corresponding tapering of the first bore portion and the needle handle.

The needle and needle guide assembly can be placed as a unit in an autoclave in order to sterlize the entire structure. Once the assembly has been sterilized, the needle remains enclosed within the assembly until needed for use. When the end caps are removed from the tubular member, the needle remains enclosed in the chamber formed by the elongated housing portion and the guide member, while only a part of the handle extends outwardly from the housing. The exposed end of the needle handle can be tapped with a finger or pushed forward so that the handle slides through the housing bore portion and into the elongated housing portion, thereby driving the needle into the skin of the patient. Once the needle is in place, the guide member and housing are disengaged, and the housing removed from the needle. The halves of the guide member then fall away, and the needle is ready for manipulation. The enlarged diameter of the handle enables the needle to be easily manipulated and accurately positioned into the desired locus. Of course, the conical shape of the guide member increases the accuracy with which the user can position the needle for insertion into the skin and the small inner diameter of the guide member makes the insertion much easier, faster and less uncomfortable.

Thus, it can be seen that the present invention avoids the need for the operator to contact the insertable portion of the needle, and avoids exposure of the insertable portion of the needle prior to insertion. Accordingly, the present invention provides an aseptic technique for performing acupuncture, improves the accuracy of applying the needle, particularly at areas of the body which are normally difficult to treat, maintains the needle in perfect structural condition and can reduce the discomfort felt by the patient during treatment.

BRIEF DESCRIPTION OF THE DRAWING

A better understanding of the present invention will be had upon reference to the following detailed description, when read in conjunction with the accompanying drawing, wherein like reference characters refer to like parts throughout the several views, and in which:

FIG. 1 is a perspective view of the preferred embodiment of the present invention;

FIG. 2 is a cross-sectional view taken along line 2—2 of FIG. 1;

FIG. 3 is a cross-sectional view taken along line 3—3 of FIG. 1;

FIG. 4 is another perspective view of the preferred embodiment of the present invention;

FIG. 5 is a cross-sectional view of the preferred embodiment of the present invention;

FIG. 6 is an exploded, partial cross-sectional view of the preferred embodiment of the present invention; and FIG. 7 is another perspective view of the preferred embodiment of the present invention.

DETAILED DESCRIPTION OF THE PREFERRED EMBODIMENT OF THE PRESENT INVENTION

Referring now to FIGS. 1, 5 and 6, a needle and needle guide assembly 10 according to the present invention are thereshown comprising an acupuncture needle 12 encased within a housing 14. The acupuncture needle 12 comprises a filiform needle 16 having a point 17, and a handle 18 opposite the point 17. The handle 18 comprises a conical portion 20 secured to an end 21 of the filiform needle 16 opposite the point 17, and a cylindrical portion 22 extending coaxially away from the point 17 of the needle 16. Preferably, the needle 16 is securely fastened to the handle 18 by embedding the needle 16 in the conical portion 20.

The handle 18 can be made in one piece and is, like the housing 14, made of a material which retains its shape when heated to sterilization tempertures in an autoclave. Preferably, the handle 18 and housing 14 are made of a nonallergenic plastic material. However, the handle 18 can also be made of metal, wood, or other suitable material. The needle 16 is preferably made of stainless steel.

Still referring to FIGS. 1, 5 and 6, the housing 14 comprises a tubular body or housing 24 and a pair of removable end caps 26 and 28. The tubular housing 24 includes a central bore 30 having a diameter greater than the widest portion of the conical handle portion 20. One end 31 of the housing forms a reduced diameter bore portion 32. The reduced diameter bore portion 32 substantially coincides with the shape of the conical handle portion 20. Accordingly, the reduced diameter bore portion 32 and the conical handle portion 20 taper radially inwardly toward the end 31 of the tubular housing 24 and the cylindrical handle portion 22, respectively. Consequently, the conical handle portion 20 can be wedged within the reduced diameter bore portion 32 and, therefore, can frictionally retain the needle 16 within a chamber 33 defined by the central bore 30 of the housing 24.

A reduced diameter peripheral portion 36 and shoulder 37 are formed on the housing 24 at the end 31. The end cap 26 includes a tubular body portion 38 and an end wall 40. The tubular body portion 38 is slidably received over the reduced peripheral portion 36. The tubular portion 38 of the end cap 26 is sufficiently long so that when an opening 42 of the end cap 26 abuts against the shoulder 37, the handle portion 22 is encased within the end cap 26 (FIG. 3) without being dislodged by the end wall 40 of the end cap 26.

A guide member 54 is inserted into and frictionally retained in an open end 56 of the housing 24 opposite the reduced bore portion 32. The guide member 54 is preferably constructed from the same material as the housing 24 and the needle handle 20, although, like those portions, wood, metal and other materials can also be employed. The guide member 54 comprises a bore portion 58 coaxial with the needle 16 and being dimensioned almost equal to but slightly greater than the diameter of the needle 16, so as to permit yet guide the longitudinal travel of the needle 16 through the bore portion 58.

The guide member 54 is characterized in that the bore portion 58 can be longitudinally breached upon disengagement of the guide member 54 from the open end 56 of the housing 24. Preferably, the guide member comprises a plurality of abutting split member portions, whose abutment (FIG. 2) is normally maintained by the insertion of the guide member 54 in the open end 56 of the housing 24. Advantageously, the abutting split member portions are two in number and comprise two half guide members 60. In the preferred embodiment the two half members 60 are identical, but they can be constructed in mirror-image fashion, or any fashion which is convenient. The preferred guide member 54 comprises a cylindrical stem portion 64 coaxial with the bore portion 58, and a cone portion 62 similarly coaxial with the bore portion 58, affixed to the stem portion 64. the stem portion 64 is inserted into the open end 56 of the housing 24, so that the point 65 of the cone 62 extends away from the housing 24. Preferably, the free end of the stem portion 64 includes a conical, outwardly flared surface 63 to facilitate assembly of the needle 16 through the guide member 54. The two half members 60 each comprise abutting sides 66, which are brought into abutment upon the insertion of the stem 64 into the open end 56 of the housing 24.

The housing 24 also includes a reduced diameter peripheral portion 48 and shoulder 49 thereon at the open end 56. The peripheral portion 48 slidably receives an end cap 28 thereon. The end cap 28 is similar to the end cap 26 and includes a tubular portion 50 and an end wall 52. The tubular portion 50 is sufficiently long so that upon abutment with the shoulder 49, a slight space is formed between the point 65 of the guide member 54 and the end wall 52 of the cap 28. Preferably, the length of the housing 24 is selected so that the point 17 of the needle 16 is received in the bore portion 58 of the guide member 54 when the conical portion 20 of the handle 18 is frictionally wedged within the reduced diameter bore portion 32 of the housing 24. The needle 16 is safely retracted from the end wall 52 of the cap 28 and is, therefore, protected from being bent by inadvertent contact with a foreign object.

The peripheral portions 36 and 48 preferably include fluid passage means between the housing 24 and the end caps 26 and 28, such as a plurality of longitudinal grooves 70 and 72, respectively, for enabling the communication of sterilizing vapor between the interior and exterior of the housing 24.

Having thus described the significant structural features of the present invention, operation of the needle and needle guide assembly 10 is easily understood. The assembled unit 10 is placed in an autoclave and heated to a sterilizing temperature. Both the inside and the outside of the assembly 10 are sterilized. The assembly 10 is removed from the autoclave when sterile for storage and later use.

When an operator desires to apply an acupuncture treatment (FIGS. 4 and 7), the end caps 26 and 28 are removed from the housing 24 (phantom in FIG. 1). The point 65 of the guide member 54 is placed in position on the desired locus of the patient's skin 67. In such a position, the needle 16 remains enclosed within the chamber 30 of the housing 24 while the cylndrical portion 22 of the handle 18 is exposed exteriorly of the housing 24. The handle 18 is tapped or pushed by the finger of the operator (FIG. 4) in order to drive the point 17 of the needle 16 out of the guide member 54 and into the acupuncture point of the patient's skin. Thus, the needle 16 is embedded in the skin without exposure to, or contact with, any contaminating materials. Moreover, once the needle has been embedded in the skin at the desired point on the skin, the narrow end of the conical bore 32 engages the cylindrical handle portion 22 to accurately guide the needle. The bore portion 58 of the guide member 54 engages the needle 16 to enhance the accuracy of insertion of the needle.

If a portion of the handle 18 of the needle 16 is permitted to remain outside the housing 24, the needle 16 can easily be manipulated by grasping the handle 18. Advantageously, however, the length of the cylindrical handle portion 22 is selected to correspond to the depth to which it is desired to introduce the needle into the patient, so that, upon insertion, the operator's finger abuts the end of the housing 24. In such a case, access to the handle 18 is had by manually disengaging the housing 24 fom the stem portion 64 of the guide member 54; the housing 24 is then removed from the needle 16 by sliding it over the handle 18 (FIG. 7). Once the stem 64 is disengaged from the handle 24, the half members 60 are no longer urged into abutment on their sides 66, and fall away freely from the needle 16. The needle is thus retained in position in the skin to insert further to an appropriate depth. Manipulation of the handle 18 and the needle 16 can then be executed without interference from the guide assembly. Any discomfort to the patient during treatment can be alleviated by a quick thrust of the needle 16 into the skin with the aid of the housing 14 as a result of a tap on the handle 18.

As a result, it can be seen that the present invention provides a means for storing, transporting and applying needles used in acupuncture treatment without subjecting the needle to exposure to, or contact with, contaminating materials, prior to insertion of the needle in the skin of the patient. The applicator also provides a convenient enclosure for protecting the needle, as well as a means for guiding the needle into the proper position on the skin of the patient. Moreover, since the structure of the present invention is rather simple and does not require complicated assembly or components, the present invention provides a disposable apparatus which can be readily sterilized after assembly, but which can be discarded after a single use.

Having the described my invention, many modifications thereto will become apparent to those skilled in the art to which it pertains, without deviation from the spirit of the present invention, as defined by the scope of the appended claims.

I claim:

1. An acupuncture needle and needle guide assembly comprising:
    a needle having a point;
    an elongated handle coaxially secured to said needle opposite said point;
    a tubular housing having a bore portion dimensioned so as to frictionally engage said handle, and an elongated portion dimensioned to enclose said needle therein;
    means for manually slidably displacing said handle in a direction towards said elongated housing portion;
    means for restricting displacement of said handle in a direction away from said elongated portion; and
    a guide member normally engaged with said elongated housing portion and having a guide passage portion substantially coaxial with said needle, said passage portion being dimensioned almost equal to but slightly greater than the diameter of said needle and allowing the longitudinal travel of said needle therein;
    wherein said guide member is disengageable from said elongated housing portion, and said guide passage is breachable throughout its length upon such disengagement of said guide member from said elongated housing portion.

2. The invention according to claim 1, wherein said housing bore portion is attached to one end of said elongated housing portion, said elongated housing portion comprises an open end portion opposite said housing bore portion, and said guide member is insertable in said open end portion of said housing.

3. The invention according to claim 2, wherein said guide member is frictionally retained in said open end portion of said housing.

4. The invention according to claim 1, wherein said guide member is fracturable.

5. The invention according to claim 1, wherein said guide member comprises a stem portion normally engaged with said elongated housing portion, and a conical portion attached to said stem portion whose point extends away from said elongated housing portion, said stem and conical portions being coaxial with said needle.

6. The invention according to claim 1, wherein said housing bore portion is attached to one end of said elongated housing portion; wherein said elongated housing portion comprises an open end portion opposite said housing bore portion; and wherein said guide member comprises a cylindrical stem portion normally insertably engaged in said open end portion of said housing, and a conical portion attached to said stem portion having a point extending away from said elongated housing portion, said stem and conical portions being coaxial with said needle.

7. The invention according to claim 5, wherein said guide member comprises a plurality of abutting split member portions, the abutment of said split portions being maintained by the insertion of said stem portion into said open end portion of said housing.

8. The invention according to claim 6, wherein said guide member comprises a plurality of abutting split member portions, the abutment of said split portions being maintained by the insertion of said stem portion into said open end portion of said housing.

9. The invention according to claim 7, wherein said plurality comprises two split member portions.

10. The invention according to claim 8, wherein said plurality comprises two split member portions.

11. The invention according to claim 1, wherein said displacing means comprises a substantially cylindrical portion on said handle coaxial with and opposite said needle, said cylindrical portion having a diameter less than but almost equal to the narrowest portion of said handle bore portion.

12. The invention according to claim 1, wherein said housing further comprises at least one end portion and an end cap insertable over said end portion.

13. The invention according to claim 12, further comprising vapor passage means intermediate said housing and said at least one cap for enabling the sterilizing steam or vapor to communicate between the interior and exterior of said housing.

14. The invention according to claim 1, wherein said housing bore portion is tapered radially inwardly in a direction away from said elongated housing portion, and said handle includes a portion tapered correspondingly to said housing bore portion.

15. The invention according to claim 14, wherein said displacing means comprises a substantially cylindrical portion on said handle coaxial with and opposite said needle, said cylinder having a diameter less than but almost equal to the diameter of the narrowest portion of said housing bore portion.

* * * * *